United States Patent [19]

Dessauer et al.

[11] Patent Number: 5,441,869
[45] Date of Patent: Aug. 15, 1995

[54] METHOD FOR THE DETERMINATION OF FIBRIN

[75] Inventors: Andreas Dessauer, Tutzing; Helmut Lill, Wielenbach; Werner Naser, Weilheim; Beatus Ofenloch-Hähnle, Haunshofen, all of Germany

[73] Assignee: Boehringer Mannheim GmbH, Mannheim-Waldhof, Germany

[21] Appl. No.: 944,691

[22] Filed: Sep. 14, 1992

[30] Foreign Application Priority Data

Sep. 25, 1991 [DE] Germany .................. 41 31 953.2
Oct. 22, 1991 [DE] Germany .................. 41 34 833.8

[51] Int. Cl.⁶ ............... G01N 33/53; G01N 33/68; G01N 33/577; G01N 33/536
[52] U.S. Cl. ................. 435/7.1; 435/7.94; 436/543; 436/548
[58] Field of Search ............. 530/388.1, 388.25; 436/548, 543; 435/7.1, 7.94

[56] References Cited

U.S. PATENT DOCUMENTS

| 4,658,022 | 4/1987 | Knowles et al. ........... 530/402 |
| 4,916,070 | 4/1990 | Matsueda et al. .......... 435/172.2 |
| 5,091,512 | 2/1992 | Gargan et al. ............ 530/387 |
| 5,120,834 | 6/1992 | Gargan et al. ............ 530/388.25 |

FOREIGN PATENT DOCUMENTS 0152612  8/1985  European Pat. Off. .
0306813  3/1989  European Pat. Off. .
0356964  3/1990  European Pat. Off. .

OTHER PUBLICATIONS

Donnelly, T. H., et al., Fibrinogen–Fibrin Conversion. II. pp. 369-383 (1954).
Chemical Abstracts, vol. 93, 201886n (1980).
Rånby, M., et al., Thrombosis Research, vol. 27, pp. 743-749 (1982).
Largo, R., et al. Blood, vol. 47, No. 6, pp. 991-1002 (1976).
Scheefers-Borchel, U. et al., Proceedings of the National Academy of Sciences (USA), vol. 82, pp. 7091-7095, 1985.
Creighton, T. E., *Proteins: Structure and Molecular Principles*, W. H. Freeman & Co., New York, New York, pp. 145-152, 1984.
Hormann, H., et al., Hoppe-Seyler's Journal of Physiological Chemistry, vol. 354, pp. 1103-1111, Sep., 1973.
Dempfle, C. E., et al., Blood Coagul. Fibrinolysis (U.K.), vol. 4, No. 1, pp. 79-86 (abstract only), 1993.

*Primary Examiner*—Stephen G. Walsh
*Attorney, Agent, or Firm*—Felfe & Lynch

[57] ABSTRACT

The present invention concerns an improved method for the determination of fibrin in body fluids in which before the actual determination the sample solution containing fibrin is incubated in the presence of thiocyanate, iodide, magnesium or/and guanidinium ions.

24 Claims, No Drawings

METHOD FOR THE DETERMINATION OF FIBRIN

The present invention concerns a process for the treatment of solutions containing fibrin which enables a more reliable determination of fibrin in body fluids and in particular an improved immunological fibrin determination by means of a heterogeneous sandwich immunoassay using a monoclonal fibrin-specific antibody.

Fibrin forms when the blood coagulation system is activated by the action of active thrombin on fibrinogen. The fibrinogen molecule consists of two pairs of $\alpha$, $\beta$ and $\gamma$ chains which are linked together by a multitude of disulfide bridges—especially in the region of the N-terminal E domain. At the N-terminal ends of fibrinogen thrombin cleaves the fibrinopeptides A from the two $\alpha$ chains and subsequently also cleaves the two fibrinopeptides B from the $\beta$ chains. The fibrin monomers which are formed are therefore denoted des-AA fibrin or fibrin I and des-AABB fibrin or fibrin II. These fibrin monomers then agglomerate and cross-link to form the fibrin clot. Soluble fibrin monomers are not usually present in blood. In contrast soluble fibrin can be detected in various coagulation disorders, especially in consumptive coagulopathy. For clinical chemistry it is therefore important to be able to reliably detect both forms of fibrin in body fluids in the presence of fibrinogen.

A specific sandwich immunoassay for the detection of fibrin using a fibrin-specific monoclonal antibody as a capture antibody has been described (Scheefers-Borchel et al., Proc. Natl. Acad. Sci. USA 82 (1985), 7091-7095). The fibrin-specific monoclonal antibody used as the capture antibody was obtained by immunization with the N-terminal hexapeptide of the $\alpha$ chain of fibrin. This peptide has the sequence Gly-Pro-Arg-Val-Val-Glu. In the above test procedure binding of fibrin to this antibody is detected with a polyclonal peroxidase-labelled <fibrinogen> antibody.

It has now been found that when fibrin in body fluids is determined by this method unexplainably low fibrin values are obtained relatively frequently or fibrin cannot be detected at all although another method for determining fibrin clearly shows the presence of fibrin.

Another problem is that values are also sometimes measured with the prior art method in samples which do not contain fibrin such as e.g. normal plasma. This is disturbing since it impedes the discrimination between zero fibrin and very low fibrin values (ca. 1 $\mu$g/ml). This obviously has particularly serious effects in automated test systems. The high blank value in normal plasma is due to the fact that fibrinogen bound adsorptively to the vessel wall is detected by the POD-labelled antibody since this is not specific for fibrin.

If one attempts to eliminate the high sample blank by using the same fibrin-specific antibody for the capture antibody as well as for the POD-labelled antibody then one finds that this is not possible. Using this test variant only "artificial" fibrin samples (fibrin standards), i.e. plasma to which fibrin solutions have been added (e.g. fibrin, dissolved in 1 mol/l NaBr solution) are detected. In contrast samples from patients which have increased fibrin values are not recognized as pathological. Thus in the method according to the state of the art it is not possible to use the same fibrin-specific antibody in a sandwich assay.

Although it is known that bromide and urea at high concentrations are indeed able to for example dissolve fibrin clots (see e.g. Rånby et al., Thrombosis Research 27 (1982), 743-749; Perlick and Bergmann, Gerinnungslaboratorium in Klinik und Praxis, Georg Thieme Verlag Leipzig 1971, p. 339; Donnelly et al., Arch. Biochem. Biophys. 56 (1955), 369-387). However, no improvement in the fibrin determination could be found after diluting fibrin solutions which had been treated in this way.

The object of the present invention was therefore to provide a process in which the disadvantages of the state of the art are at least partially eliminated and in particular the reliability and sensitivity of the fibrin determination are improved.

The object according to the present invention is achieved by a process for the treatment of a solution containing fibrin which is characterized in that thiocyanate, iodide, magnesium or/and guanidinium ions are added to the solution and it is incubated. The concentration of the aforementioned ions is preferably chosen to be high enough to irreversibly bring the fibrin molecules in the sample solution into a form which is amenable to immunological determination, presumably by dissolving complexes or aggregates.

Surprisingly it is possible to achieve a considerably more reliable determination of fibrin in body fluids by treating solutions containing fibrin according to the present invention. The present invention therefore in addition concerns a method for the determination of fibrin in body fluids which is characterized in that thiocyanate, iodide,. magnesium or/and guanidinium ions are added to the sample solution containing fibrin before carrying out the determination, it is incubated, if desired diluted after the incubation and subsequently the fibrin content of the sample solution is determined.

It was surprisingly found that treatment of sample solutions containing fibrin with thiocyanate, iodide, magnesium or/and guanidinium ions considerably improves the accessibility of the fibrin so that a considerable increase in the sensitivity of the fibrin test can be achieved. It is particularly surprising that only a few quite special substances are suitable for this. For example it turned out that chloride, bromide, arginine and urea are not suitable.

When carrying out the method of determination according to the present invention fibrin is also found in plasma samples in which the well-known method according to Scheefers-Borchel et al. does not work but in which pathological fibrin values were measured with a third method. This third method is the FM test of Boehringer Mannheim GmbH. This is an agglutination test which uses fibrin-coated erythrocytes (Largo et al., Blood 47 (1976), 991). When fibrin is present in a sample the erythrocytes agglutinate and thus enable a semi-quantitative fibrin test. The sensitivity of this test is $\geq 10$ $\mu$g/ml which is relatively low, nevertheless positive results are often obtained with this test while the immunological test according to Scheefers-Borchel indicates no fibrin or an amount of $<<10$ $\mu$g/ml.

The duration and temperature of the incubation in the process according to the present invention are usually not particularly critical. However, it is expedient to incubate the solution for 1 to 60 minutes, preferably for 15 to 30 minutes after addition of the ionic substances at a temperature of 10° to 40° C., preferably 15° to 30° C. At lower incubation temperatures there is usually a corresponding increase in the incubation period.

If the solution containing fibrin is incubated with thiocyanate ions then the thiocyanate is preferably added to the sample solution in the form of alkali metal, magnesium or ammonium thiocyanate solutions. For this it is advantageous that the concentration of thiocyanate ions in the sample solution is more than 0.5 mol/l and is preferably between 0.5 and 8.5 mol/l and particularly preferably between 0.7 and 7 mol/l whereby even when the thiocyanate concentrations are high there is no detection of fibrinogen i.e. increased fibrin values do not occur when determining normal plasma. The use of thiocyanate ions is particularly preferred for carrying out the process according to the present invention.

If the sample solution containing fibrin is incubated with iodide ions then these are preferably added in the form of alkali metal, magnesium or ammonium iodide solutions. It is expedient that the concentration of iodide ions in the sample solution exceeds 1 mol/l and is preferably between 2 and 8 mol/l and particularly preferably between 2 and 4 mol/l In addition it was found that a synergistic effect is observed when the solution is incubated with a combination of thiocyanate and iodide ions i.e. the combination of both ions exceeds the sum of the individual effects. In such an embodiment of the process according to the present invention the concentration of thiocyanate ions is preferably between 0.2 and 2 mol/l and the concentration of iodide ions is preferably between 2 and 8 mol/l The concentration of thiocyanate ions is particularly preferably between 0.5 and 1.5 mol/l and the concentration of iodide ions is particularly preferably between 3 and 4 mol/l The range 0.5 to 1.0 mol/l is quite especially preferred for thiocyanate ions.

When the sample solution is incubated with guanidinium ions these are preferably added in the form of guanidinium hydrohalide solutions particularly preferably guanidinium hydrochloride solutions. The concentration of guanidinium ions in the solution should exceed 1 mol/l and is preferably between 1 and 4 mol/l When the sample solution containing fibrin is incubated with magnesium ions these are preferably added in the form of soluble magnesium salts e.g. magnesium halides or magnesium nitrate. It is advantageous that the concentration of magnesium ions in the sample solution be at least 0.5 mol/l, preferably between 1 and 3 mol/l and particularly preferably between 1 and 2 mol/l The treatment according to the present invention of a solution containing fibrin results in an increase in the sensitivity of a subsequent fibrin determination. After the incubation step according to the present invention and before the actual determination it has in general proven to be necessary to dilute the sample solution because of the high salt concentration present during the incubation. For this the sample solution is preferably diluted with a suitable buffer in a ratio of 1:5 to 1:500 of sample solution to buffer, particularly preferably of 1:10 to 1:200. It should be noted that merely using dilute solutions of the substances suitable according to the present invention is not suitable for releasing fibrin from complexes but rather that it is in general necessary for the detachment that the substances be allowed to act on the sample in a high concentration in order to cause the release of fibrin. It is only possible to dilute afterwards.

In this process it was found that improved results are obtained in the fibrin determination when the pH value of the sample solution is adjusted to a range of 5.5 to 7.5 and preferably to a range of 5.8 to 6.2 after the incubation step according to the present invention.

As a result of the sample dilution after the incubation with a suitable buffer in which the pH value of the sample solution is particularly preferably adjusted to pH 6.0, fibrin I and fibrin II are detected equally well. 0.1 mol/l phosphate buffer pH 6.0 has for example proven to be a suitable buffer. Good results were, however, also obtained with an acetate and a citrate buffer. The action of the buffer is therefore not due to a specific effect of the phosphate ions but instead the pH value has an effect.

The adjustment of the sample solution to a pH value between 5.5 and 6.5 can in principle also be achieved by using a conventional laboratory acid, however, it is more practical to use buffer as the diluting reagent whose buffer capacity has to be sufficiently strong to ensure a pH value of 5.5 to 6.5, particularly preferably of 6.0, after mixing with the plasma. Already at pH values of <5.5 markedly increased values i.e. false positive values are also found in plasma without fibrin (e.g. normal plasma).

The last step in the method according to the present invention for the determination of fibrin in body fluids comprises the determination of the fibrin content of the sample solution. This step is preferably carried out by immunological methods in particular using at least one fibrin-specific monoclonal antibody.

In a particularly preferred embodiment the fibrin content of the sample solution is determined by a heterogeneous sandwich assay in which the sample solution is brought into contact with an immobilized or an immobilizable fibrin-specific first antibody and a labelled second antibody which can bind to a conjugate of fibrin and the first antibody and the label is determined in a known manner.

The first antibody is immobilized or immobilizable i.e. it is present bound to a solid phase or it is modified in such a way that it is capable of binding to a solid phase. Examples of immobilized antibodies are those which are attached to the surface of a solid phase, e.g. a plastic carrier, according to methods known to one skilled in the art. Such an immobilization can for example be carried out by non-covalent adsorption or by covalent coupling of the antibody to reactive groups or/and spacer molecules on the surface of the solid phase. An example of an immobilizable antibody is a biotinylated antibody which is capable of binding to a solid phase coated with streptavidin. The production of biotinylated antibodies is usually carried out in such a way that a reactive biotin derivative is reacted with SH groups of the antibody to form the biotinylated antibody. Instead of an antibody, antibody fragments such as F(ab)$_2$, Fab or Fab' fragments can be used for this (F. Fieber, "Biotinylierung monoklonaler Antikörper in: Monoklonale Antikörper/Herstellung und Charakterisierung", Springer-Verlag Berlin, Heidelberg, New York (1990) 299–302).

The first antibody must be a fibrin-specific antibody i.e. it should have no significant reactivity towards fibrinogen molecules. Fibrin-specific monoclonal antibodies can be produced by immunizing laboratory animals with the hexapeptide Gly-Pro-Arg-Val-Val-Glu according to the state of the art. An example of a fibrin-specific monoclonal antibody which can be used in the process according to the present invention is the antibody 2B5 (ECACC 89112802) which was obtained by immunizing laboratory animals with the heptapeptide Gly-Pro-Arg-Val-Glu-Arg. For the immunization, the peptide is used in a known manner bound to carrier proteins such as KLH (keyhole limpet hemocyanin) (Proc. Natl. Acad. Sci. USA 78 (1981) 3404).

The second antibody is a labelled antibody which can react with the conjugate of the first antibody and fibrin. The label on this antibody can for example be an enzymatic, fluorescent, luminescent, radioactive or NMR-active group. Examples of such marker groups are known to one skilled in the art. The antibody preferably carries an enzymatic marker group e.g. peroxidase (POD) or alkaline phosphatase. The POD labelling can for example be carried out according to Wilson and Nakane, Recent developments in the periodate method of conjugating horseradish peroxidase (HRPO) to antibodies, in: Immunofluorescence and related staining techniques, (W. Knapp, L. Holubar, and G. Wick, eds.), Elsevier/North-Holland Biomedical Press, pages 215–224.

The second antibody can be the same antibody as the first antibody i.e. it can have an identical binding site. On the other hand the second antibody can be different from the first antibody. For example antibodies are also suitable as the second antibody which recognize fibrinogen as well as fibrin. Such an antibody is e.g. the antibody 1.156.317 (ECACC No. 89060902). Furthermore the second antibody can also be a polyclonal antibody or an antibody fragment.

A further immunological test procedure for which the method of sample preparation according to the present invention is suitable, is a test using latex. In this latex test, latex particles which have antibodies to fibrin on their surface become attached to fibrin (which has two identical epitopes) which leads to an aggregation and the turbidity can be measured. Suitable test procedures are described for example in J. Clin. Immunoassay 13 (1990), 127–131 and EP-A 0356 964.

Finally it should also be pointed out that the incubation according to the present invention of a solution containing fibrin with thiocyanate, iodide, magnesium or guanidinium ions can to a certain extent be dependent on the subsequent method for determining the fibrin content in the sample solution. Thus in automated tests using the same fibrin-specific antibody as the immobilized and as the labelled antibody and when the streptavidin/biotin technology is used, thiocyanate concentrations of 1.5 to 6.5 mol/l in the sample solution are well suited. A thiocyanate concentration of 4.0 mol/l is particularly preferred. If a fibrin-specific immobilized antibody and a second unspecific labelled antibody is used without streptavidin/biotin, a concentration range of 0.7 to 1.5 mol/l thiocyanate in the sample solution is well suited. About 1.2 mol/l thiocyanate is particularly preferably used for the incubation of the sample.

The invention in addition concerns a reagent kit which contains the thiocyanate, iodide, magnesium or/and guanidinium salts in a solid or/and dissolved form.

The antibodies 2B5 and 1.156,317 were deposited according to the provisions of the Budapest Treaty with the deposit numbers ECACC 89112802 and ECACC 89060902 at the ECACC, Porton Down, GB.

It is intended to further elucidate the invention by the following examples.

EXAMPLE 1

Determination of fibrin with an immobilized fibrin-specific antibody and an unspecific, POD-labelled antibody.

a) General notes:

If not stated otherwise the antibody-POD conjugates were dissolved with conjugate buffer and adjusted to a concentration of 80–120 mU/ml peroxidase activity. Complete IgGs are not used but rather the Fab fragments.

b) Test procedure (general)

In the first incubation step a specific antibody is immobilized to a plastic carrier (NUNC microtitre plates). In order to prevent unspecific bindings, the non-saturated binding sites of the solid phase are saturated by a recoating medium. In the second incubation step this antibody binds to the fibrin from the sample (first immune reaction). The fibrin has two antigenic determinants for this. In the subsequent immune reaction with POD-labelled fibrin antibodies sandwich complexes are formed (second immune reaction). The amount of the sandwich complexes formed is a measure for the concentration of fibrin in the sample. In the subsequent washing step (bound-free separation) the non-bound POD conjugate is removed. After addition of chromogen (ABTS ®, the POD activity bound to the tube wall is determined photometrically. A reference curve is established for each measurement series for the evaluation. For this a fibrin standard solution is diluted with sample dilution solution and pretreated according to example 1d part a.

c) Reagents

Coating solution

52 $\mu$g/ml MAB 2B5 in buffer solution

Buffer solution 137 mmol/l NaCl,
2.68 mmol/l KCl
8.09 mmol/l $Na_2HPO_4$
1.47 mmol/l $KH_2PO_4$,
pH 7.3

Washing buffer

Buffer solution, containing 0.05% Tween ® 20

Recoating solution

1% casein, 3 mol/l urea in buffer solution

Sample dilution solution 0.1 mol/l phosphate buffer, pH 6.0; 0.05% Tween ® 20

Conjugate solution

Conjugate of POD and MAB 1.156.317 (POD activity: 0.085 U POD/ml) in 0.035 mol/l sodium phosphate,
0.154 mol/l NaCl,
1% polyethyleneglycol 40000,
0.2% bovine serum albumin,
0.05% Tween ® 20, pH 7.4

Substrate solution 0.95 mg ABTS ®/ml (2,2'-azino-di(3-ethylbenzthiazolinesulfonate-6) in 0.06 mol/l disodiumhydrogen phosphate,
0.04 mol/l citric acid, 3.3 mmol/l sodium perborate, pH 4.5

Sample incubation solution:

2.4 mol/l potassium thiocyanate, if not stated otherwise.

Fibrin standard

100 $\mu$g/ml fibrin I in sample dilution solution.

Further standard dilutions are prepared by diluting with sample dilution solution.

d) Sample

Sample collection (citrate plasma)

9 parts freshly collected blood are mixed with 1 part anticoagulant and subsequently centrifuged for 10 minutes at 2000 g (ca. 3000 rpm on a normal laboratory centrifuge). The supernatant is removed with a pipette.

Then the procedure is as described i.e.:

Sample preparation a) Variant without the above-mentioned salts:

1 part sample is mixed with 100 parts sample dilution solution. This mixture is denoted sample solution in the following.

b) Variant with the above-mentioned salts:

1 part sample is mixed with 1 part sample incubation solution (e.g. KSCN, 2.4 mol/l) and incubated for 30 minutes at room temperature. This mixture is denoted sample solution in the following.

Thus the concentration of thiocyanate, iodide, magnesium and/or guanidinium ions in the sample incubation solution is double that of the sample solution. Then one part of this solution is diluted with 50 parts sample dilution solution (phosphate buffer, pH 6.0; in relation to the 1+1 mixture).

e) 0.1 ml coating solution is added to each well of a microtitre plate. It is shaken for 30 min at room temperature, emptied and 0.15 ml recoating solution is added. After shaking for 15 min at room temperature it is washed twice with 0.3 ml washing buffer each time.

0.1 ml sample prepared according to example 1 (d) is added per well. It is shaken for 30 min at room temperature and washed three times with 0.3 ml washing buffer each time. 0.1 ml POD-labelled antibody is added, shaken for 15 min at room temperature and washed four times with 0.3 ml washing buffer each time. 0.1 ml substrate solution is added, shaken for 15 min at room temperature and the absorbance is determined at 410 nm.

Wavelength: 410 nm
Reference wavelength: 490 nm
Measurement: against reagent blank f) Construction of the calibration curve A fibrin standard solution (100 μg/ml) is used for the calibration.

Mixing table:

| μg/ml fibrin | Concentrations of the fibrin standard dilutions | | | | |
|---|---|---|---|---|---|
| | 0 | 10 | 25 | 50 | 75 | 100 |
| Fibrin standard 100 μg/ml | — | 10 μl | 25 μl | 50 μl | 75 μl | 100 μl |
| Sample dilution solution | 100 μl | 90 μl | 75 μl | 50 μl | 25 μl | — |

All standard dilutions must be pretreated or diluted as the samples before use in the test.

g) Fibrin determination after sample preparation according to the present invention A substantial increase in the sensitivity of the fibrin test is achieved by addition of thiocyanate ions to the sample solution (Table 1).

Traces of thrombin (50 mU thrombin per 10 ml plasma) were added to human citrate plasma and after 10 min 2.0 USP units heparin per ml plasma were added in order to inhibit the thrombin activity. In order to determine an initial value, thrombin was pipetted into plasma containing heparin (0 min value). The samples were then pretreated analogously to example 1d.

TABLE 1

Increase in the sensitivity of the fibrin test in plasma using thiocyanate.

| Predilution of the sample with thiocyanate. Thiocyanate concentration in the sample solution (mol/l) | Thrombin treated plasma | |
|---|---|---|
| | 0 min[1] ΔA/10 min[2] | 10 min[1] ΔA/10 min[2] |
| without thiocyanate | 0.004 | 0.384 |
| 1.5 | 0.021 | 0.753 |
| 1.4 | 0.042 | 1.180 |
| 1.3 | 0.064 | 1.722 |
| 1.2 | 0.074 | 1.795 |
| 1.1 | 0.062 | 1.738 |
| 1.0 | 0.055 | 1.549 |
| 0.9 | 0.030 | 0.916 |
| 0.8 | 0.011 | 0.484 |
| 0.7 | 0.004 | 0.408 |
| 0.6 | 0.003 | 0.368 |
| 0.5 | 0.001 | 0.379 |

[1] Duration of the thrombin action
[2] ΔA/10 min: Change in absorbance within 10 minutes Result: Incubating the sample with thiocyanate results in an increase in the sensitivity of the fibrin test in plasma over a wide concentration range.

The sample pretreatment with guanidinium hydrochloride also improves the sensitivity of the fibrin test (Table 2).

The sample preparation and the method of determination were carried out analogously to the experiments with the addition of thiocyanate.

TABLE 2

Increase in the sensitivity of the fibrin test in plasma using guanidinium hydrochloride.

| Predilution of the sample with guanidinium.HCl Guanidinium.HCl concentration in the sample solution (mol/l) | Thrombin treated plasma | |
|---|---|---|
| | 0 min[1] ΔA/10 min[2] | 10 min[1] ΔA/10 min[2] |
| 0.00 | 0.004 | 0.598 |
| 1.75 | 0.061 | 0.999 |
| 1.70 | 0.110 | 0.937 |
| 1.65 | 0.075 | 0.952 |
| 1.60 | 0.148 | 0.883 |
| 1.55 | 0.132 | 1.083 |
| 1.50 | 0.144 | 1.011 |
| 1.45 | 0.106 | 1.238 |
| 1.40 | 0.075 | 1.344 |
| 1.35 | 0.059 | 1.379 |
| 1.30 | 0.056 | 1.148 |
| 1.25 | 0.042 | 0.815 |

[1],[2] cf. Table 1

In a further experiment blood was collected from a healthy person without first adding an anticoagulant. At the times indicated in Table 3, an anticoagulant was added to aliquots of the collected blood (9 parts blood +1 part anticoagulant consisting of 0.11 mol/l trisodium citrate; 200 IU/ml heparin; 0.02 mol/l ε-aminocaproic acid, 0.33 mg/100 ml aprotinin). They were subsequently centrifuged and the plasma obtained was used for the fibrin test. The anticoagulant prevents the activation of the coagulation system. Coagulation proteases, in particular thrombin, which are already present are inactivated by heparin. Thus after addition no further fibrin can be formed and the plasma sample is preserved in its individual activation condition. ε-aminocaproic acid and aprotinin prevent an activation of the fibrinolytic system and thus counteract degradation of the fibrin which has already been formed at the respective time.

(A) Dilution of the sample according to example 1d, part a.

(B) Pretreatment of the sample with thiocyanate analogous to example 1d, part b (2.4 mol/l potassium thiocyanate in the sample incubation solution, 15 min incubation at room temperature).

TABLE 3

Activation of blood by leaving it to stand without anticoagulant.

| Time of addition of the anticoagulant (min) | Dilution of the plasma samples according to variant | |
|---|---|---|
| | (A) A/10 min | (B) A/10 min |
| 0 | 0.014 | 0.097 |
| 5 | 0.011 | 0.105 |
| 10 | 0.020 | 0.112 |
| 17.5 | 0.057 | 0.167 |
| 20 | 0.222 | 0.609 |
| 22.5 | 0.352 | 1.015 |

Result: Addition of thiocyanate to the sample results in a significant increase in the sensitivity of the test signal.

EXAMPLE 2

Immunological determination of fibrin with immobilized biotinylated fibrin-specific antibody and peroxidase-(POD)-labelled antibody A fibrin-specific monoclonal antibody is used in biotinylated form; streptavidin-coated reaction vessels (produced according to EP-A 0 269 092) are used.
Reagents Biotinylated antibody, working solution: 1.3 μg/ml conjugate of antibodies 2B5 and biotin in 0.085 mol/l potassium dihydrogen phosphate, 0.015 mol/l dipotassium hydrogen phosphate, 0.5% bovine serum albumin, 0.05% Tween ® 20.

Washing solution: 4.3 mmol/l sodium chloride.

POD conjugate solution: conjugate of antibody 2B5 and POD [POD activity 0.139 U/ml] in 0.035 mol/l sodium phosphate, 0.154 mol/l NaCl, 1% polyethylene glycol 40000, 0.2% bovine serum albumin, 0.05% Tween ® 20, pH 7.4.
Substrate solution (ABTS ®):

0.95 mg ABTS ®/ml in 0.06 mol/l disodium hydrogen phosphate, 0.04 mol/l citric acid, 3.3 mmol/l sodium perborate, pH 4.5.
Procedure for the determination:

20 μl sample is pretreated according to example 1d (for concentrations of thiocyanate, iodide or guanidinium hydrochloride cf. tables). 1 ml working solution of the biotinylated antibody is added, incubated for 30 min at room temperature and the emptied reaction vessels are washed twice with washing solution.

1 ml POD conjugate solution is added, incubated for 30 min at room temperature and the emptied reaction vessels are washed twice with washing solution.

1 ml substrate solution is added, incubated for 30 min at room temperature and the colour formed is determined at 405 nm.

TABLE 4

Detection of fibrin in plasma with and without addition of thiocyanate

| Sample Standard concentration [μg/ml] | without thiocyanate | | with thiocyanate, (6 mol/l in the sample incubation solution) | |
|---|---|---|---|---|
| | Absorbance mA/30 min | Recovery of fibrin in the sample μg/ml | Absorbance mA/30 min | Recovery of fibrin in the sample μg/ml |
| 0 | 12 | | 19 | |
| 1 | 41 | | —[1] | |
| 5 | 146 | | — | |
| 10 | 315 | | — | |
| 25 | 802 | | — | |
| 50 | 1787 | | 2110 | |
| Path. plasma 1 | 37 | 0.9 | 2769 | 69.8 |
| Path. plasma 2 | 43 | 1.1 | 1154 | 34.6 |
| Path. plasma 3 | 8 | 0 | 386 | 12.5 |
| Path. plasma 4 | 127 | 4 | >4000 | >100.0 |
| Normal plasma 1 | 14 | 0 | 8 | 0 |
| Normal plasma 2 | 18 | 0 | 7 | 0 |

[1]: not determined

Without addition of thiocyanate, fibrin is only detected in fibrin standards i.e. in samples which were obtained by supplementing normal plasma with fibrin solutions in 1 mol/l NaBr solution.

In contrast when thiocyanate is used for the sample preparation fibrin is also detected in the patient samples. The sample blank (normal plasma) is also very low in the pretreatment with thiocyanate ions. This shows that fibrinogen is not also detected when the sample is pretreated with thiocyanate ions.

TABLE 5

Dependence of the fibrin test on the thiocyanate concentration.

| | Absorbance (mA/30 min) Thiocyanate ion concentration in the sample solution (mol/l) | | | |
|---|---|---|---|---|
| Sample | 1.5 | 3.0 | 4.0 | 5.0 |
| Standard 0 | 21 | 22 | 18 | 22 |
| Standard 1 μg/l | 61 | 67 | 72 | 69 |
| Standard 50 μg/ml | 1921 | 2009 | 2047 | 2055 |
| Normal plasma 3 | 28 | 43 | 43 | 46 |
| Normal plasma 4 | 27 | 62 | 75 | 74 |
| Path. plasma 5 | 514 | 1083 | 1337 | 1376 |
| Path. plasma 6 | 107 | 1230 | 1560 | 1569 |

At the thiocyanate concentrations used the measured values are not falsified for example by fibrinogen.

In a further experiment it could be demonstrated that the concentration of the thiocyanate ions can be increased to 6.5 mol/l in the sample solution without causing an error in the measured values.

TABLE 6

Dependence of the test signal on the duration of the sample incubation with thiocyanate (4 mol/l thiocyanate in the sample solution).

| | Absorbance (mA/30 min) Incubation period (min) | | | | |
|---|---|---|---|---|---|
| Sample | 1 | 3 | 5 | 10 | 30 |
| Fibrin standard 50 μg/ml | 2228 | 2104 | 2038 | 2087 | 1942 |
| Path. plasma No. 7 | 487 | 776 | 978 | 1094 | 1062 |

TABLE 6-continued

Dependence of the test signal on the duration of the sample incubation with thiocyanate (4 mol/l thiocyanate in the sample solution).

| Sample | Absorbance (mA/30 min) Incubation period (min) | | | | |
|---|---|---|---|---|---|
| | 1 | 3 | 5 | 10 | 30 |
| Path. plasma No. 8 | 312 | 687 | 514 | 1050 | 925 |
| Path. plasma No. 9 | 658 | 1555 | 1257 | 1719 | 1552 |
| Path. plasma No. 10 | 922 | 1159 | 1170 | 1257 | 1318 |

The determination of fibrin can already be carried out a short time after the sample pretreatment, preferably 15 to 30 min after addition of the thiocyanate solution. This is also shown by Table 7.

TABLE 7

Dependence of the measurement signal on the duration of the sample pretreatment (thiocyanate 4 mol/l in the sample solution).

| Sample | Incubation period (min) | Absorbance (mA/30 min) | Fibrin concentration (found) (μg/ml) |
|---|---|---|---|
| Normal plasma No. 5 | 15 | 112 | 0.8 |
| | 20 | 126 | 1.1 |
| | 28 | 125 | 1.1 |
| | 38 | 111 | 0.8 |
| | 51 | 111 | 0.8 |
| | 66 | 91 | 0.4 |
| Pathol. plasma No. 11 | 21 | 1162 | 30.7 |
| | 26 | 1192 | 31.5 |
| | 34 | 1209 | 31.9 |
| | 44 | 1105 | 29.3 |
| | 57 | 1110 | 29.4 |
| | 72 | 1088 | 28.8 |
| Fibrin standard (50 μg/ml) | 30 | 2075 | 50.0 |
| | 46 | 1877 | 46.4 |
| | 56 | 1955 | 47.8 |
| | 69 | 1968 | 48.1 |
| | 84 | 1688 | 42.6 |

TABLE 8

Comparison of the sample incubation with thiocyanate and guanidinium hydrochloride

| Sample preparation | Example 1d, Part a | | Thiocyanate[2] (8 mol/l) | | Guanidine.HCl[2] (3 mol/l) | |
|---|---|---|---|---|---|---|
| | Absorbance A/30 min | Fibrin (found) μg/ml | Absorbance A/30 min | Fibrin (found) μg/ml | Absorbance A/30 min | Fibrin (found) μg/ml |
| Standard 0 | 0.030 | | 0.039 | | 0.031 | |
| Standard 1 μg/ml | 0.112 | | 0.089 | | 0.082 | |
| Standard 5 μg/ml | 0.427 | | 0.283 | | 0.311 | |
| Standard 10 μg/ml | 0.776 | | 0.532 | | 0.506 | |
| Standard 25 μg/ml | 1.560 | | 1.087 | | 1.129 | |
| Standard 50 μg/ml | 2.792 | | 1.955 | | 2.126 | |
| Plasma, 13 min activated | 0.067 | 0.36 | 0.860 | 18.73 | 0.284 | 4.74 |
| Plasma, 16 min activated | 0.077 | 0.45 | 2.179 | 57.02 | 0.585 | 11.66 |
| Pathological patient sample | —[1] | — | 1.923 | 49.04 | —[1] | — |

[1]: not determined
[2]: in the sample incubation solution

The activated plasma samples were obtained analogously to the method for the experiment described in Table 3 by allowing whole blood to stand for a period of 13 or 16 min.

The experiment shows that the sample preparation with guanidinium hydrochloride and thiocyanate leads to an improvement in the fibrin test.

In a further experiment the effect of the addition magnesium ions on the sensitivity of the fibrin test in plasma was examined. The results are shown in Table 9.

TABLE 9

Effect of magnesium nitrate on the sensitivity of the fibrin test in plasma.

| | Concentration of magnesium nitrate in the sample incubation solution | | | | | |
|---|---|---|---|---|---|---|
| | 1.0 mol/l | | 1.5 mol/l | | 2.0 mol/l | |
| Sample | A/30 min | Fibrin μg/ml | A/30 min | Fibrin μg/ml | A/30 min | Fibrin μg/ml |
| Standard 0 | 0.031 | | 0.032 | | 0.031 | |
| Standard 1 | 0.100 | | 0.068 | | 0.070 | |
| Standard 5 | 0.381 | | 0.221 | | 0.207 | |
| Standard 10 | 0.747 | | 0.464 | | 0.420 | |
| Standard 25 | 1.569 | | 0.889 | | 0.855 | |
| Standard 50 | 2.823 | | 1.603 | | 1.689 | |
| normal plasma | 0.042 | 0.17 | 0.040 | 0.29 | 0.038 | 0.20 |
| normal plasma | 0.027 | 0.02 | 0.032 | 0.16 | 0.030 | 0.08 |

TABLE 9-continued

Effect of magnesium nitrate on the
sensitivity of the fibrin test in plasma.

Concentration of magnesium nitrate in the
sample incubation solution

| | 1.0 mol/l | | 1.5 mol/l | | 2.0 mol/l | |
|---|---|---|---|---|---|---|
| Sample | A/30 min | Fibrin µg/ml | A/30 min | Fibrin µg/ml | A/30 min | Fibrin µg/ml |
| Path. plasma | 0.352 | 4.35 | 0.276 | 5.78 | 0.426 | 11.05 |

EXAMPLE 3

Improvement of the fibrin test by incubation with iodide or a combination of thiocyanate and iodide.

Pathological plasma samples which reacted positive in the reference method according to Largo, were pretreated as described in Example 1d). The determination of fibrin was carried out as stated in Example 2. Table 10 shows the recovery of fibrin after incubation with iodide, thiocyanate and a combination of iodide and thiocyanate.

TABLE 10

Recovery of fibrin in pathological plasma
samples after incubation with different
sample incubation solutions.

The following sample incubation solutions were compared:
8 mol/l K thiocyanate
7.5 mol/l Na iodide,
7.5 mol/l Na iodide + 0.98 mol/l (= 9.5%) thiocyanate

| | 8 mol/l KSCN | | 7.5 mol/l NaI | | 7.5 mol/l NaI + 0.98 mol/l KSCN | |
|---|---|---|---|---|---|---|
| Sample | A/30 min[1] | µg/ml | A/30 min | µg/ml | A/30 min | µg/ml |
| Std. 0 | 0.033 | | 0.032 | | 0.051 | |
| Std. 1 | 0.083 | | 0.098 | | 0.102 | |
| Std. 5 | 0.311 | | 0.337 | | 0.320 | |
| Std. 10 | 0.550 | | 0.632 | | 0.564 | |
| Std. 25 | 1.246 | | 1.380 | | 1.181 | |
| Std. 50 | 2.286 | | 2.546 | | 2.199 | |
| Plasma 1 | 0.217 | 3.3 | 0.213 | 2.8 (84%) | 0.228 | 3.1 (93%) |
| Plasma 2 | 1.258 | 25.3 | 0.937 | 16.0 (63%) | 1.122 | 23.4 (92%) |
| Plasma 3 | 0.516 | 9.3 | 0.385 | 5.7 (62%) | 0.455 | 7.9 (84%) |
| Plasma 4 | 0.639 | 11.8 | 0.498 | 7.7 (66%) | 0.568 | 10.4 (87%) |
| Plasma 5 | 1.683 | 35.2 | 1.357 | 24.4 (69%) | 1.596 | 35.1 (99%) |
| Plasma 6 | 2.282 | 49.9 | 1.766 | 33.0 (66%) | 1.937 | 43.5 (87%) |
| Plasma 7 | 0.521 | 9.4 | 0.368 | 5.4 (58%) | 0.548 | 9.9 (106%) |
| Plasma 8 | 1.154 | 23.0 | 0.880 | 14.9 (65%) | 1.009 | 20.7 (90%) |
| Plasma 9 | 2.205 | 47.9 | 1.804 | 33.8 (71%) | 1.838 | 41.1 (85%) |
| Plasma 10 | 1.025 | 20.1 | 0.842 | 14.2 (71%) | 0.970 | 19.8 (98%) |
| Plasma 11 | 1.431 | 29.3 | 1.225 | 21.7 (74%) | 1.342 | 28.8 (98%) |
| Plasma 12 | 0.937 | 18.2 | 0.824 | 13.8 (76%) | 0.829 | 16.4 (90%) |
| Plasma 13 | 1.158 | 23.1 | 0.882 | 15.0 (65%) | 1.105 | 23.0 (99%) |

[1]A/30 min: Change in absorbance after 30 minutes

Table 10 shows that in combination thiocyanate and iodide complement each other synergistically. This effect is only achieved to about 70% with 7.5 mol/l NaI alone. (Std.=standard;—the numbers show the fibrin value in µg/ml). (Plasma samples 1 to 13: the figures in parentheses in percent show the recovery of fibrin (µg/ml) in relation to pretreatment of the sample with 8 mol/l thiocyanate ions).

TABLE 11

Combination of 7.5 mol/l sodium iodide[1] with
9.5% (0.98 mol/l) potassium thiocyanate[1].

| Sample | KSCN (8 mol/l) | NaI (7.5 mol/l) | KSCN (0.98 mol/l) | NaI (7.5 mol/l) + KSCN (0.98 mol/l) |
|---|---|---|---|---|
| | Change in absorbance in 30 minutes | | | |
| Plasma 1(+) | 0.864 | 0.572 | 0.008 | 0.730 |
| Plasma 2(+) | 0.624 | 0.408 | 0.008 | 0.596 |
| Plasma 3(+) | 2.124 | 1.714 | 0.038 | 1.876 |
| Plasma 4(+) | 0.520 | 0.324 | 0.018 | 0.472 |

[1]concentration of the sample incubation solution

Table 11 shows that an increase in the measured signal can be achieved with 7.5 mol/l sodium iodide compared with 5.0 mol/l sodium iodide (cf. Table 12) and that 0.98 mol/l thiocyanate does not have a significant effect.

TABLE 12

Combination of iodide with thiocyanate
Pathological plasma samples were mixed 1 + 1 with the
stated solutions and incubated for 30 min. The further
test procedure was carried out as in Example 2.

| | Change in absorbance in 30 minutes | | |
|---|---|---|---|
| Sample | NaI[1] (5 mol/l) | KSCN[1] (0.98 mol/l) | NaI[1] + KSCN[1] (5 mol/l) (0.98 mol/l) |
| Plasma 1 | 0.120 | 0.008 | 0.408 |
| Plasma 2 | 0.176 | 0.016 | 0.890 |
| Plasma 3 | 0.060 | 0.008 | 0.210 |
| Plasma 4 | 0.814 | 0.038 | 1.458 |
| Plasma 5 | 0.122 | 0.018 | 0.252 |

[1]concentration of the sample incubation solution

The combination of both ions at the stated concentrations results in a synergistic effect.

We claim:

1. Process for improving the sensitivity of a fibrin assay which uses a fibrin specific capture monoclonal antibody, comprising;
    (a) adding at least one ion selected from the group consisting of a thiocyanate ion, an iodide ion, a magnesium ion, and a guanidinium ion to a sample containing fibrin in an amount sufficient to increase the selectivity of said fibrin specific capture monoclonal to fibrin,
    (b) incubating said sample,
    (c) contacting said sample with said fibrin specific capture monoclonal antibody, and
    (d) determining a reaction between said fibrin specific capture monoclonal antibody and fibrin, whereby said reaction corresponds to the quantity of fibrin in the sample.

2. Process of claim 1, wherein said ion is a thiocyanate ion added to said sample in the form of an alkali metal thiocyanate, magnesium thiocyanate, or ammonium thiocyanate.

3. Process of claim 2, comprising adding said thiocyanate ion in an amount such that the concentration of said thiocyanate ion in said sample is between 0.7 and 8.5 mol/l.

4. Process of claim 1, wherein said ion is an iodide ion added to said sample in the form of an alkali metal iodide, magnesium iodide, or ammonium iodide.

5. Process of claim 4, comprising adding said iodide ion in an amount such that the concentration of said iodide ion in said sample is between 1 and 8 mol/l.

6. Process of claim 1, comprising adding iodide ion and a thiocyanate ion to said sample.

7. Process of claim 6, comprising adding said iodide ion in an amount such that the concentration of said iodide ion in said sample is from 2 to 8 mol/l and adding said thiocyanate ion in an amount such that the concentration of said thiocyanate ion in said sample is from 0.2 to 2 mol/l.

8. Process of claim 1, comprising adding a guanidinium ion in the form of guanidinium hydrochloride.

9. Process of claim 8, comprising adding said guanidinium ion in an amount such that the concentration of said guanidinium ion in said sample is from 1 to 4 mol/l.

10. Process of claim 1, comprising adding said magnesium ion in the form of a soluble magnesium salt.

11. Process of claim 10, comprising adding said soluble magnesium salt in an amount such that the concentration of said magnesium salt in said sample is from 0.5 to 3 mol/l.

12. Process of claim 1, comprising incubating said sample for from 1 to 60 minutes.

13. Process of claim 1, comprising incubating said sample at a temperature of from 10° to 40° C.

14. Method of claim 1, comprising diluting said sample following incubation.

15. Method of claim 1, comprising adjusting pH of said sample to a pH of from 5.5 to 7.5 following incubation.

16. Method of claim 15, comprising adjusting pH to from 5.8 to 6.2.

17. Method of claim 15, comprising adding a buffer to said sample following incubation to achieve said pH from 5.5 to 7.5, in a ratio of from 1:5 to 1:500 of sample to buffer.

18. Method of claim 1, comprising determining fibrin by first contacting said sample with said fibrin specific capture monoclonal antibody, and thereafter contacting said sample with a labelled antibody agent which specifically binds to said fibrin, determining a second reaction between said labelled antibody agent and fibrin bound to said fibrin specific capture monoclonal antibody, whereby said second reaction provides a measure of said first reaction between said fibrin specific capture monoclonal antibody and said fibrin in said sample.

19. Method of claim 18, wherein said fibrin specific capture monoclonal antibody is immobilized.

20. Method of claim 18, further comprising immobilizing said fibrin specific capture monoclonal antibody.

21. Method of claim 18, wherein said fibrin specific capture monoclonal antibody is a biotinylated monoclonal antibody or biotinylated monoclonal antibody fragment.

22. Method of claim 18, wherein said labelled antibody agent is an enzyme labelled antibody or enzyme labelled antibody fragment.

23. Method of claim 18, wherein the specificity of said fibrin specific capture monoclonal antibody and said labelled antibody agent differ from each other.

24. Method of claim 18, wherein the specificity of said fibrin specific capture monoclonal antibody and said labelled antibody agent is the same.

* * * * *